United States Patent [19]
McMurray

[11] Patent Number: 6,016,687
[45] Date of Patent: Jan. 25, 2000

[54] APPARATUS FOR INDICATING OZONE EXPOSURE

[76] Inventor: Larry Daniel McMurray, 14421 29th Ave. S., SeaTac, Wash. 98168

[21] Appl. No.: 09/126,260

[22] Filed: Jul. 30, 1998

Related U.S. Application Data

[63] Continuation-in-part of application No. 08/701,120, Aug. 21, 1996, Pat. No. 5,788,930.
[51] Int. Cl.[7] ............................... G01N 7/00; G01N 9/00; G01N 21/00
[52] U.S. Cl. ........................... 73/23.2; 73/31.018; 422/58
[58] Field of Search .................................. 73/23.2, 31.01, 73/31.02; 422/90, 83, 50, 53, 55, 107

*Primary Examiner*—Hezron Williams
*Assistant Examiner*—Jay L. Politzer
*Attorney, Agent, or Firm*—Mark Zovko

[57] ABSTRACT

A device using the failure of a material decomposable by ozone to indicate a predetermined ozone exposure. In the preferred embodiment, a plurality of contact rods stretch latex to varying thicknesses to indicate more than one level of ozone exposure upon failure. The device can be made compact and portable, usable as a personal monitor. In an alternative embodiment, material such as rubber in the shape of O-rings is employed as the material decomposable by ozone.

12 Claims, 12 Drawing Sheets

WITHOUT OZONE DECOMPOSE-VAPOR CYCLE

OPEN SWITCH

*Fig. 6A*

CLOSED SWITCH

APPARATUS FOR INDICATING OZONE EXPOSURE

CROSS RELATION TO OTHER APPLICATIONS

This application is a continuation-in-part of U.S. Ser. No. 08/701,120 filed Aug. 21, 1996 and issuing as U.S. Pat. No. 5,788,930 on Aug. 4, 1998.

BACKGROUND OF THE INVENTION

1. Field of the Invention

This application relates in general to apparatus for producing ozone for the elimination of chemical odor, germs, and other organic particulate matter in an enclosed space, and more particularly to ozone generating apparatus using sensors which allow the personal safety, efficient purification, and damage prevention associated with well known adverse effects of ozone overexposure in an enclosure.

2. Description of the Prior Art

Ozone generating apparatus has a long history in the prior art. The present application focuses on a portable ozone generating device such as that disclosed in U.S. Pat. No. 4,863,701 issued to the present inventor on Sep. 5, 1989. In that device, ozone was generated by electrostatic discharge using an array of glass tubes each containing a conductive rod serving as a core. Adjacent tubes were parallel to each other and the conductive rod of each tube is connected to the secondary terminal of a high voltage transformer. The tubes containing the conductive rods serve as an electrode when the voltage transformer is activated thereby creating an electrostatic field. Oxygen molecules in the electrostatic field are transformed to form ozone molecules. This prior art apparatus can be applied to deodorizing an enclosed space with the addition of a fan to feed oxygen past the tube array and distribute the ozone that is generated. After the ozone generation cycle stops, and to reduce excess ozone concentration in the enclosure, the apparatus had an odor emitting chamber which opened allowing a substance of choice causing breakdown of ozone molecules present. In this apparatus the ozone decomposing substance, intended to be a pleasant scent such as any one of the a number of perfumed scents, was released at the end of the ozone generating cycle in the same amount regardless of the amount of ozone present. A major drawback would occur if the ozone concentration in the enclosure after deodorizing was high enough to break down the perfumed scent and remain at a high level. Monitoring of the ozone level in the enclosure or the level of perfumed scent did not occur, nor was control of the ozone generating cycle relative to the release of the ozone decomposing vapor present.

A search of the prior art has revealed several patents with the last decade which attempt to monitor the ozone generating cycle.

| U.S. Pat. No. | Inventor | Issue Date |
| --- | --- | --- |
| 5,368,816 | Detzer | 11/26/94 |
| 5,266,275 | Faddis | 11/30/93 |
| 5,256,377 | Nakamaru, et al | 10/26/93 |
| 4,842,829 | Hirai, et al | 6/27/89 |
| 4,853,735 | Kodama, et al | 8/1/89 |

Generally, these patents differ from the present invention which provides an air and surface antiseptic purifying system using ozone and electronic logic circuitry used to monitor operating cycles according to feedback from sensors. Apparatus used to purify enclosures has strict safety considerations as ozone in suitable germicidal concentration can be harmful to human or animal life. (See 21 CFR 801.415) It is imperative that ozone generating apparatus to be successfully employed have safeguards built-in to the apparatus which assure its fail safe operation. Each of the above patent has a safe use of ozone generating apparatus as a goal but the individual embodiments differ from applicant. For example, in U.S. Pat. No. 5,368,816 issued to Detzer, ozone is added to a stream of air circulating through an air conditioning system to oxidize pollutants. A filter downstream of the ozone generating device is used to decompose any ozone after this operation. Sensors further downstream detect if the ozone concentration of the conditioned are as below a minimum safety level. Applicant's device, in contrast, does not require a filter, nor a sensor which detects ozone over a preset level resulting in a shut down of the entire system. The other patents in the search differ in structural and/or functional features relative to the present application and are cited of interest in a general nature. The teachings of these patents alone or in combination, would not anticipate or render obvious applicant's invention as later claimed in this application.

A major problem in ozone application in an enclosure continues to be possible damage due to ozone concentrations over a period of time. Ozone is known to cause premature aging of rubber items, plant foliage and other material affected by oxidation. A device set to run 12 hours in an enclosure may take only two hours to purify that environment with ozone, or may take twelve hours depending on the pollutants and odor present in the enclosure. It is desired to find an apparatus which will produce only enough ozone required to purify the environment without exposing the susceptible contents of the enclosure to ozone degradation. The present invention seeks to solve this problem.

With respect to indicators of hazardous unseen materials, the prior art contains devices which, for example, change color when exposed to various chemicals. Also electronic monitors which are relatively expensive are known. These indicators may require matching a color which can be problematic for those who have difficulty discerning colors or the very young. The present invention overcomes these difficulties and provides a simple and easily readable device.

SUMMARY OF THE INVENTION

The present invention has as its purpose the safe and efficient purification of an enclosures, such as a structured building or vehicle. An ozone generating device is provided for producing a source of ozone in the enclosure such as the apparatus generally described in U.S. Pat. No. 4,863,701 issued to the present inventor. An ozone decomposing material is also available which can be introduced into the enclosure if preset limits on the ozone exposure level in the enclosure are exceeded. To trigger the introduction of the ozone decomposing material a control system is used which includes an ozone sensor to monitor the ozone concentration in the enclosure and electronic logic circuitry to feedback the output from the ozone sensor to a controlling device which can initiate release of the ozone decomposing material into the enclosure. The ozone sensor may be remote to the ozone generator which is contemplated to be portable and within the enclosure. In one embodiment of the invention, the control system can include a contact switch which is held closed by spring action similar to automotive ignition points. A material which decomposes in the presence of ozone can be placed between the two contact surfaces of the switch thus holding the switch open by acting as an insulator until the material decomposes and fails in the ozone rich environment. A useful material for this purpose is latex such as that used in surgical gloves. The contact switch of this control system also can be used as a self limiting switch to terminate ozone treatment at a predetermined exposure thereby preventing unwanted damage due to excessive ozone exposure.

In an alternative embodiment of the invention, the apparatus can have an ozone generator and an ozone decomposing material available for release after the ozone generating cycle is complete. The control system of this embodiment includes a sensor for sensing a pre-set level of the ozone decomposing material as in theory, the molecules of the ozone decomposing material such as propane molecules will react with residual ozone until the ozone is consumed. At this point the sensor which can be designated a "combustion" sensor will sense a pre-set concentration of propane molecules present and stop the further release of propane molecules into the enclosure.

The sensor in this embodiment may be located outside of the ozone generating apparatus.

Two other embodiments of the invention are noteworthy. First, to safeguard the enclosure during purification, a motion sensor can be used which would detect any motion within the boundaries of the enclosure such as the inadvertent entrance of a person. The motion sensor would feedback to the ozone generating apparatus to stop the production of ozone until the apparatus is reset. The motion sensor could also, upon detection of motion within the enclosure, send a signal to introduce ozone decomposing vapor normally used after the ozone cycle is completed. Secondly, yet another embodiment contemplates remote control of the apparatus from a point outside of the enclosure. The ozone generating apparatus and ozone decomposing material capable of being released are located as before within the enclosure. The controls for controlling the ozone production cycle and the controls for releasing the ozone decomposing material are located outside of the enclosure. Sensing devices would signal readings to an operator outside of the enclosure. The operator can proceed with the purification of the enclosure and subsequent release of ozone decomposing material while maintaining a high degree of control over both of these functions. Also, it is possible for the ozone decomposing material module to be located separate from the ozone generator.

In another embodiment of the present invention, a device for indicating the level of ozone exposure using a material which decomposes in the presence of ozone is disclosed. A sheet of latex can be stretched using a rod contacting the latex. As the latex is stretched, its thickness decreases and the level of ozone concentration over time to produce failure of the latex is diminished. A plate can be made having the latex over openings in the plate and otherwise fastened down, The plate may have several openings each with a different length rod forcing the latex to stretch depending on the length of the rod. Different levels of ozone exposure, therefore, can be measured as the thickness of the latex in each opening will vary with failure occurring at different exposure levels. A spring can be used in this embodiment in conjunction with the rod that will force one end of the rod through the plate at failure of the latex thereby giving a visible indicator of a given ozone exposure. The device can be made compact and portable so that it can be carried on one's person during walking or exercise. If a predetermined harmful level of ozone is present, a visible indicator on the device will warn the user.

As a variation, rubber O-rings can be used instead of latex. Two plates are provided each having a peg thereon. The O-ring fits over each peg and the plates can be moved apart to stretch the O-ring a predetermined amount. Multiple peg and O-ring combinations wherein the pegs are spaced at varying distances will provide an indicator of multiple ozone exposures.

It is, therefore, an object of the present invention to provide a safe, effective apparatus for purifying an enclosure using electronic logic as part of a control system.

Another object of the present invention is to provide an apparatus which prevents high residual ozone levels in an enclosure after purification.

A further object of the present invention is to provide a portable ozone generating apparatus for purifying a closed environment.

Yet another object of the present invention is to provide safeguards to an ozone generating apparatus which responds directly to high residual ozone levels in an enclosure.

Another object of the present invention is to provide a ozone generating apparatus which uses a latex switch to determine when a critical ozone exposure has been reached, thereby preventing damage to the contents of the enclosure.

Another object of the present invention is to provide a compact and portable indicator of ozone exposure. Still another object of the present invention is to provide an ozone exposure indicator which indicates more than one predetermined level of ozone.

These and other objects and advantages will become more apparent from the subsequent detailed description especially when taken in conjunction with the drawings.

DETAILED DESCRIPTION OF THE PREFERRED EMBODIMENT

Figure 1:
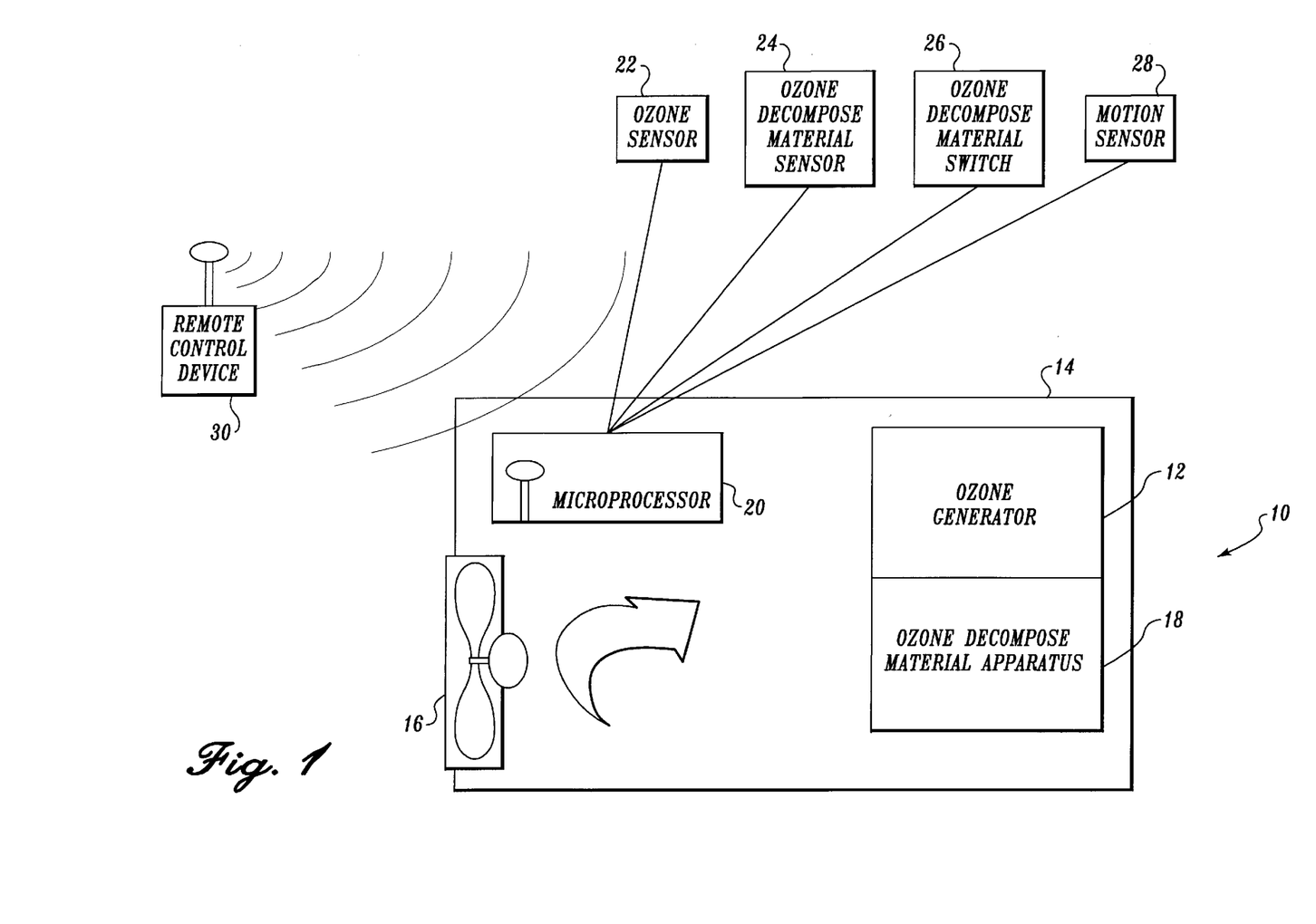
FIG. 1 is a schematic diagram of the apparatus of the present invention.

Referring to the Figures, the present invention can be described in detail. FIG. 1 shows schematically an apparatus for purifying an environment generally designated as 10. Purifying apparatus 10 has an ozone source or ozone generator 12 which can be similar to the apparatus disclosed in U.S. Pat. No. 4,863,701 issued to the present inventor. The ozone generator can be housed in housing 14 having a fan 16 to distribute ozone to the environment surrounding the apparatus 10. Also, enclosed in the housing 14 is an ozone decomposing material device 18 which is capable of emitting at the appropriate time to the environment surrounding apparatus 10, a material which decomposes ozone present in the environment over time. As part of the internal logic circuitry in the apparatus 10, a microprocessor 20 is provided within housing 14. The microprocessor can be connected to various sensors including an ozone sensor 22 and an ozone decomposing material sensor 24. Output from the ozone sensor 22 is fed to the microprocessor 20 and can be used to shape the ozone generation cycle. Similarly, the ozone decomposing material sensor 24 inputs to the microprocessor which in turn can control the release of ozone decomposing material to the environment to be purified. The microprocessor 20 can be a microprocessor well known in the art. Also, both the ozone sensor 22 and ozone decomposing material sensor 24 can be located integrally with the apparatus 10 or remote to the apparatus 10 using well known adaptations. The ozone decomposing material cycle may include a switch 26 which is open during the part of the purifying cycle that ozone decomposing material is not needed and closed during that portion of the cycle when ozone decomposing material is needed. In an optional embodiment, a motion sensor 28 can be provided which would sense any motion in the environment due to the inadvertent entry of a moving being into that environment. The motion sensor can be a standard well known variety with its output connected to the microprocessor 20. In this embodiment, the entry of a human into the environment would immediately stop ozone generation and initiate ozone decomposing material release if the entry occurred during the ozone generating cycle. As yet another option the entire apparatus 10 can be placed in an enclosed environment and controlled with a remote control device 30 from outside of the environment. Such a remote control device again, would be standard in the art and operate, for example, on a radio frequency. In this way, manual override to the apparatus 10 is provided in a safe, effective manner.

Figure 2:
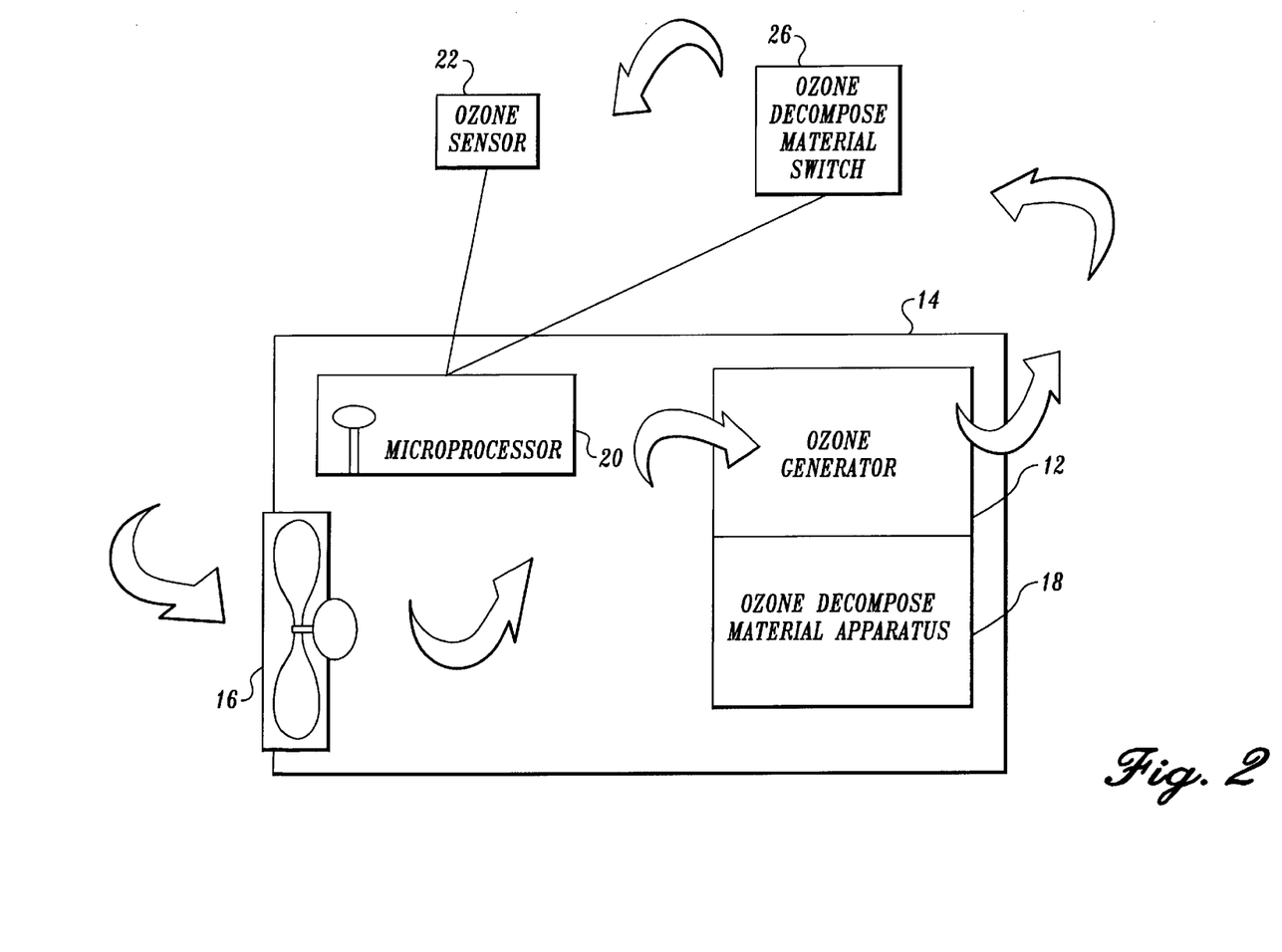
FIG. 2 is a schematic flow diagram showing the interplay between the generation of ozone and the ozone decomposing material switch.
Figure 3:
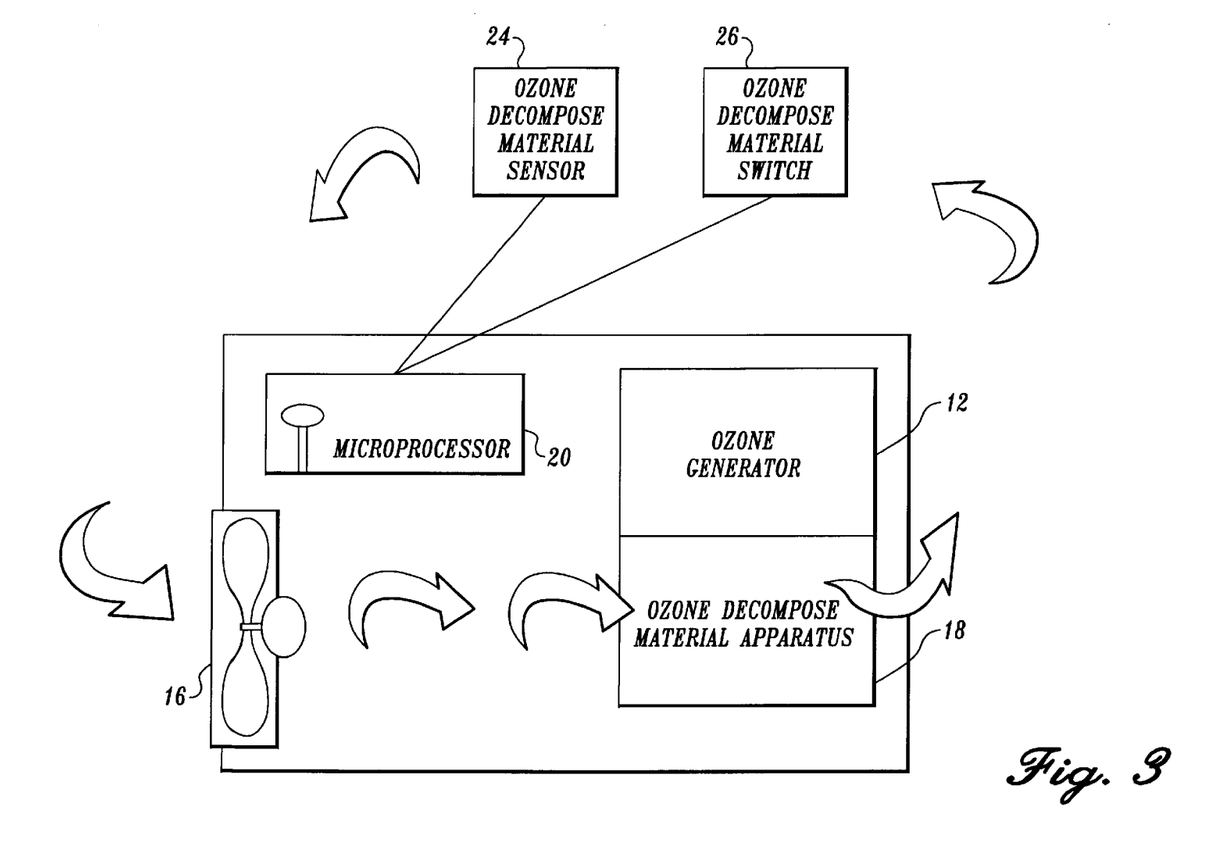
FIG. 3 is a schematic flow diagram showing the ozone decomposing material cycle.
Figure 4:
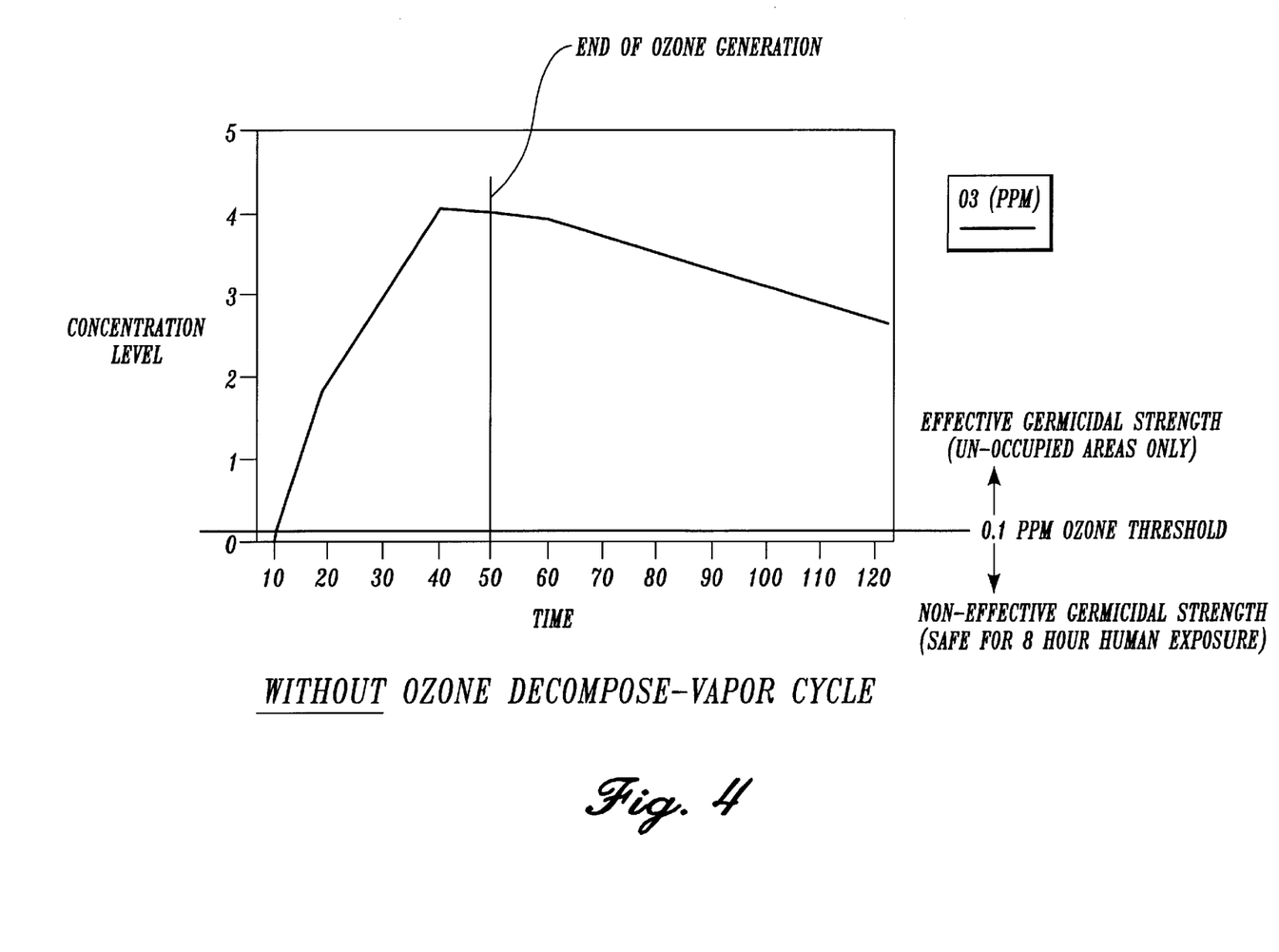
FIG. 4 shows a graph of ozone concentration vs. time for the ozone generating cycle of the present invention.
Figure 5:
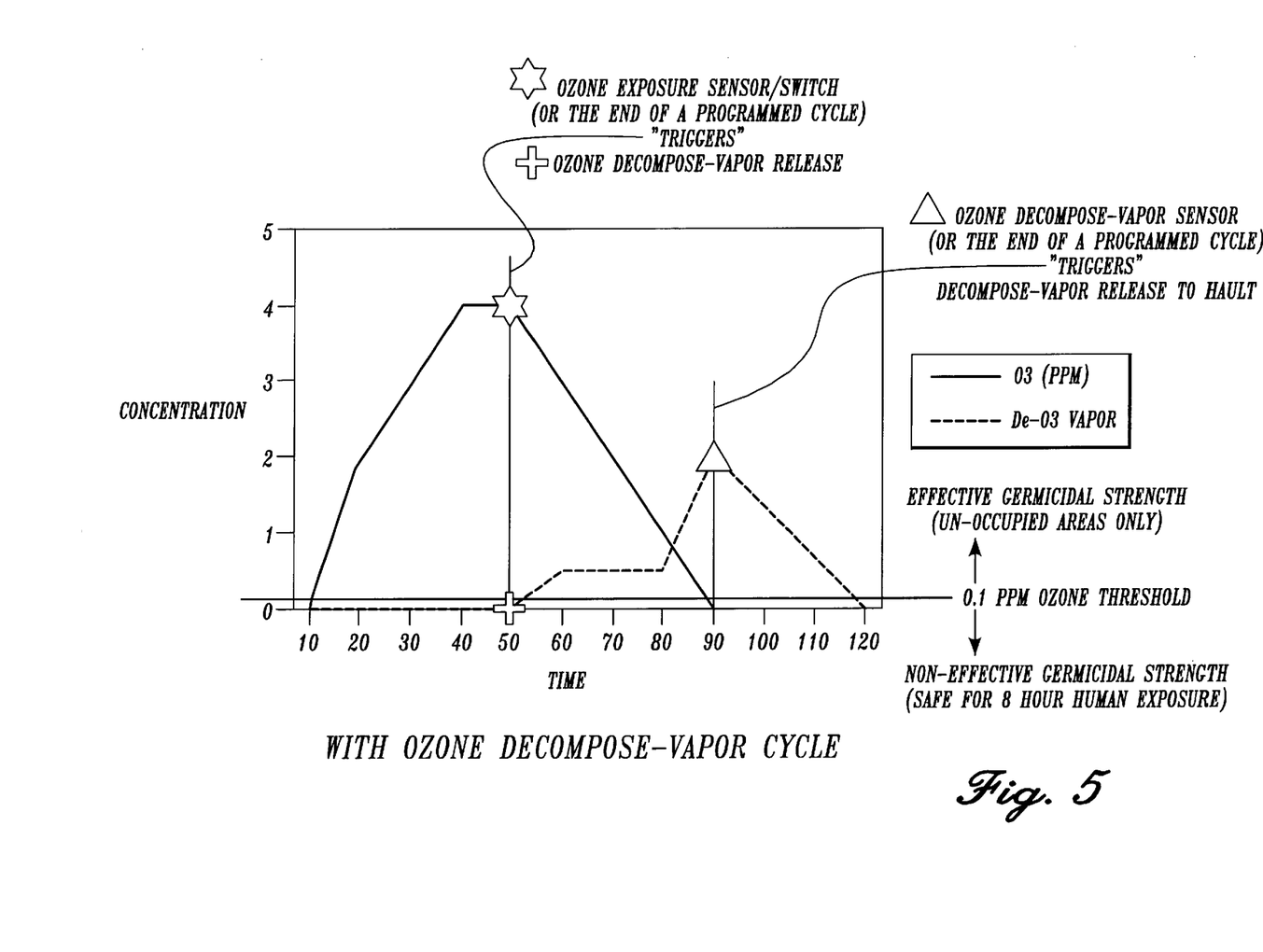
FIG. 5 shows a graph of concentration vs. time for an ozone generating cycle and an ozone decomposing cycle of the present invention.

Referring now to FIGS. 2 and 3, the flow of ozone generated in the apparatus 10 by ozone generator 12 to the surrounding environment during the ozone generating cycle is shown. FIG. 3 shows the ozone decomposing material cycle occurring after switch 26 has closed due to the appropriate signal from the ozone decomposing material sensor 24 or a pre-set ratio determined by the microprocessor 20 logic circuitry. These two cycles shown are controlled by the microprocessor 20 and/or by receiving signals from the sensors 22 and 24. FIG. 4 shows a graph of the ozone generating cycle using an ozone generator 12 alone without a ozone decomposing material release cycle. The graph shows ozone concentration in a typical environment to be purified over time. The peak antiseptic level ozone exposure occurs at shut-off (50 minutes) and gradually decreases to about 3 PPM at 120 minutes. If 0.1 PPM is a safe level for human exposure it is seen that the environment even after 2 hours ozone is still significantly present in the environment making human entry to that environment unsafe. Referring to FIG. 5, if the ozone decomposing cycle is added using an apparatus 10 described above, significantly different results occur. At 50 minutes, it is assumed that the ozone generating cycle is concluded either due to predetermined programming or to the output from an ozone exposure sensor. At this point, the ozone decomposing material is released to the environment being purified and the concentration of that material increases over the next 40 minutes to a peak at 90 minutes. During this time, the ozone concentration in the environment has dropped below a 0.1 PPM threshold making the environment safe for 8 hour human exposure. At 90 minutes in the example shown, entry of the ozone decomposing material to the environment being purified is halted either by predetermined programming or due to the output of a sensor (such as sensor 24 in FIG. 1) to the microprocessor of the apparatus. As shown in the graph of FIG. 5, the ozone decomposing material dissipates relatively rapidly over the next 30 minutes to a negligible concentration. The overall result is that the environment is purified by ozone, the ozone remaining from the ozone generating cycle is broken down by release of an ozone decomposing material, and the residual concentration of the ozone decomposing material falls to a negligible amount in a relatively short time.

Figure 6A:
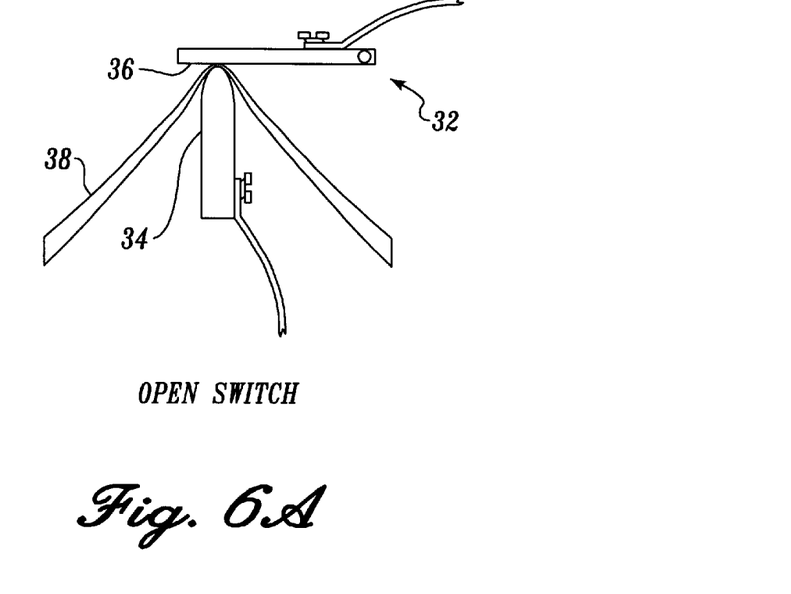
FIG. 6A shows a switch using a barrier for holding the switch open which is susceptible to ozone decomposition.
Figure 6B:
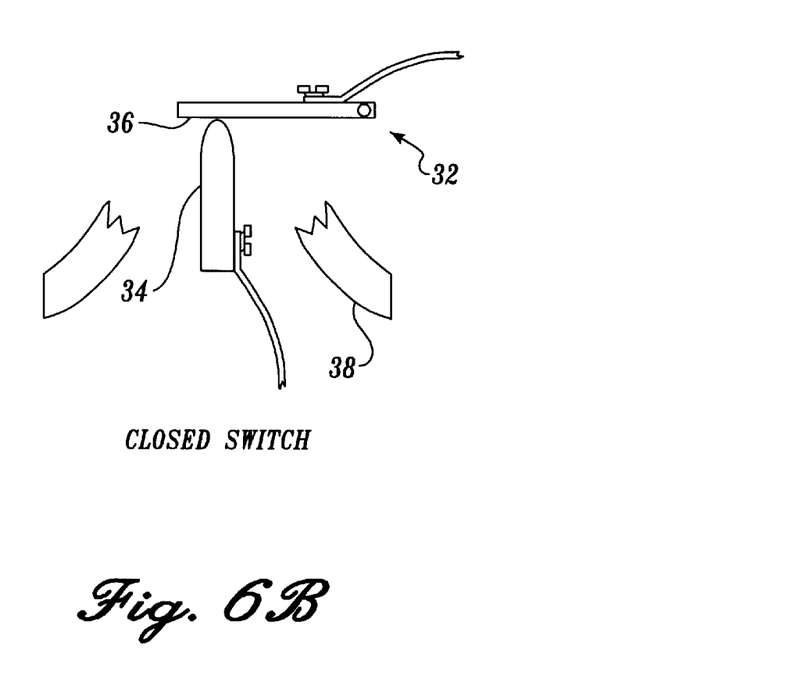
FIG. 6B shows the switch of FIG. 6A having the barrier broken thereby closing the switch.

Referring to FIGS. 6A and 6B an ozone decomposing material switch such as switch 26 of FIG. 1 is shown. This switch designated generally as 32, has a contact 34 and a contact 36 separated by a material 38 which is degradable by ozone; such as latex. In the normal mode the switch 32 is prevented from being closed by the presence of material 38. After degradation over time by ozone, the material 38 will fail, thereby allowing switch 32 to close due to contacts 34 and 36 touching. This switch 32 can be used to initiate the introduction of the ozone decomposing material into the environment to be purified by acting as an ozone exposure sensor.

The ozone decomposing material used in conjunction with the present invention can include a variety of organic materials. It is well known that any organic molecules will break down ozone, however, it is obvious that certain organic materials are more suitable than others in this application. One such recommended material is odorless propane which is available readily. This material works effectively to break down ozone molecules, does not impart undesirable odors, and is harmless to most environments and their contents.

Figure 7:
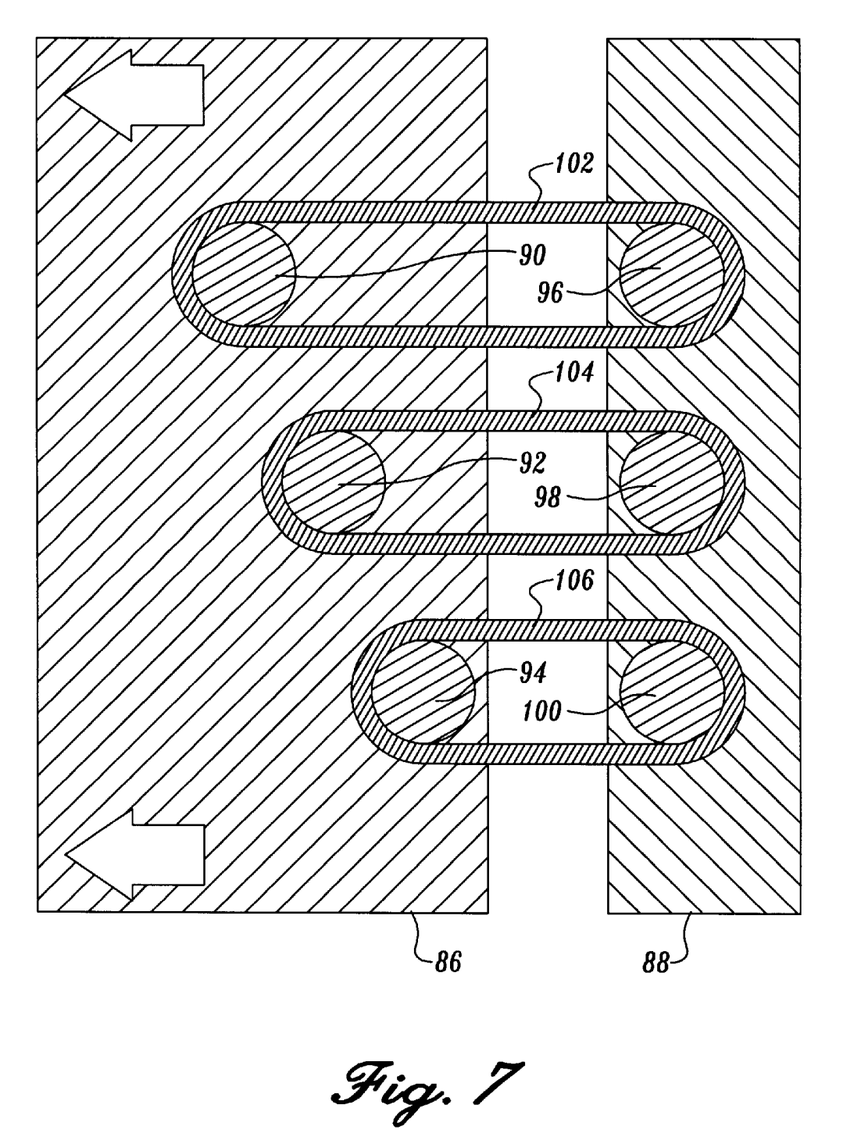
FIG. 7 shows a schematic of an indicator using O-rings prior to ozone exposure.
Figure 8:
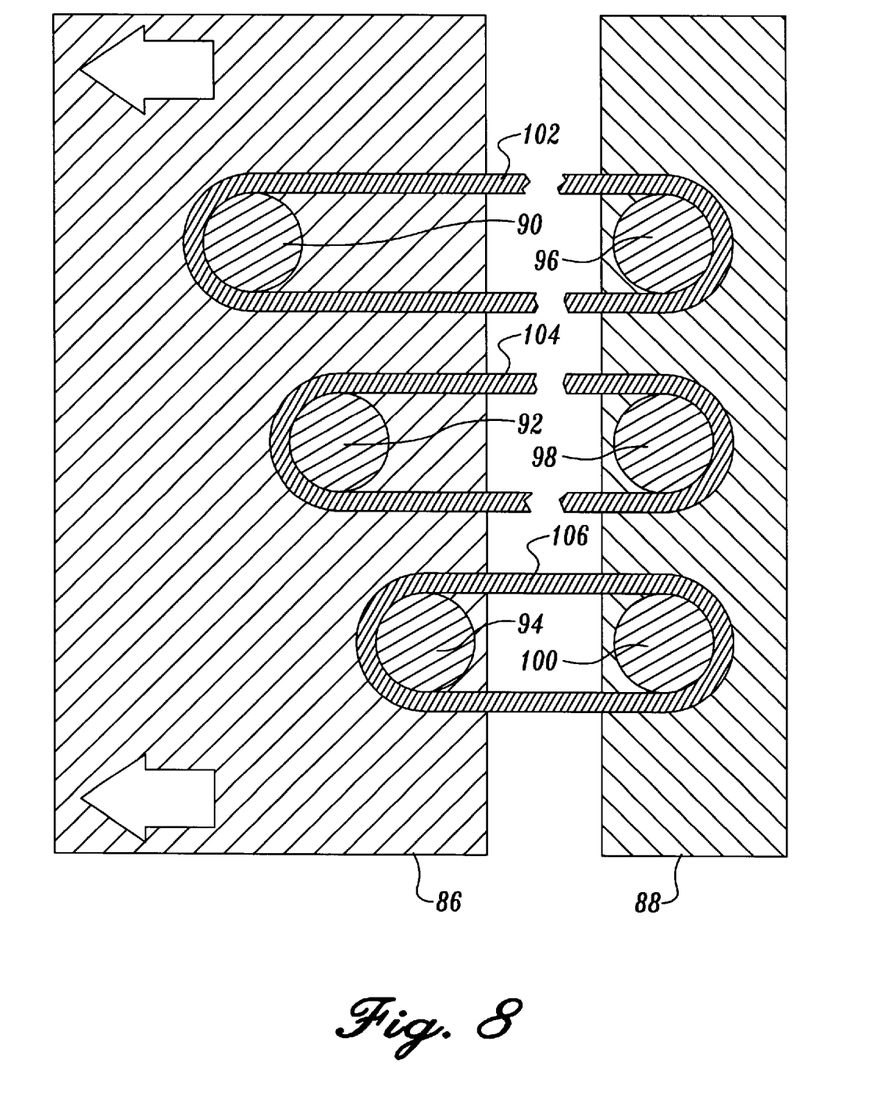
FIG. 8 shows a schematic of the indicator of FIG. 7 after the O-rings have failed.
Figure 9:
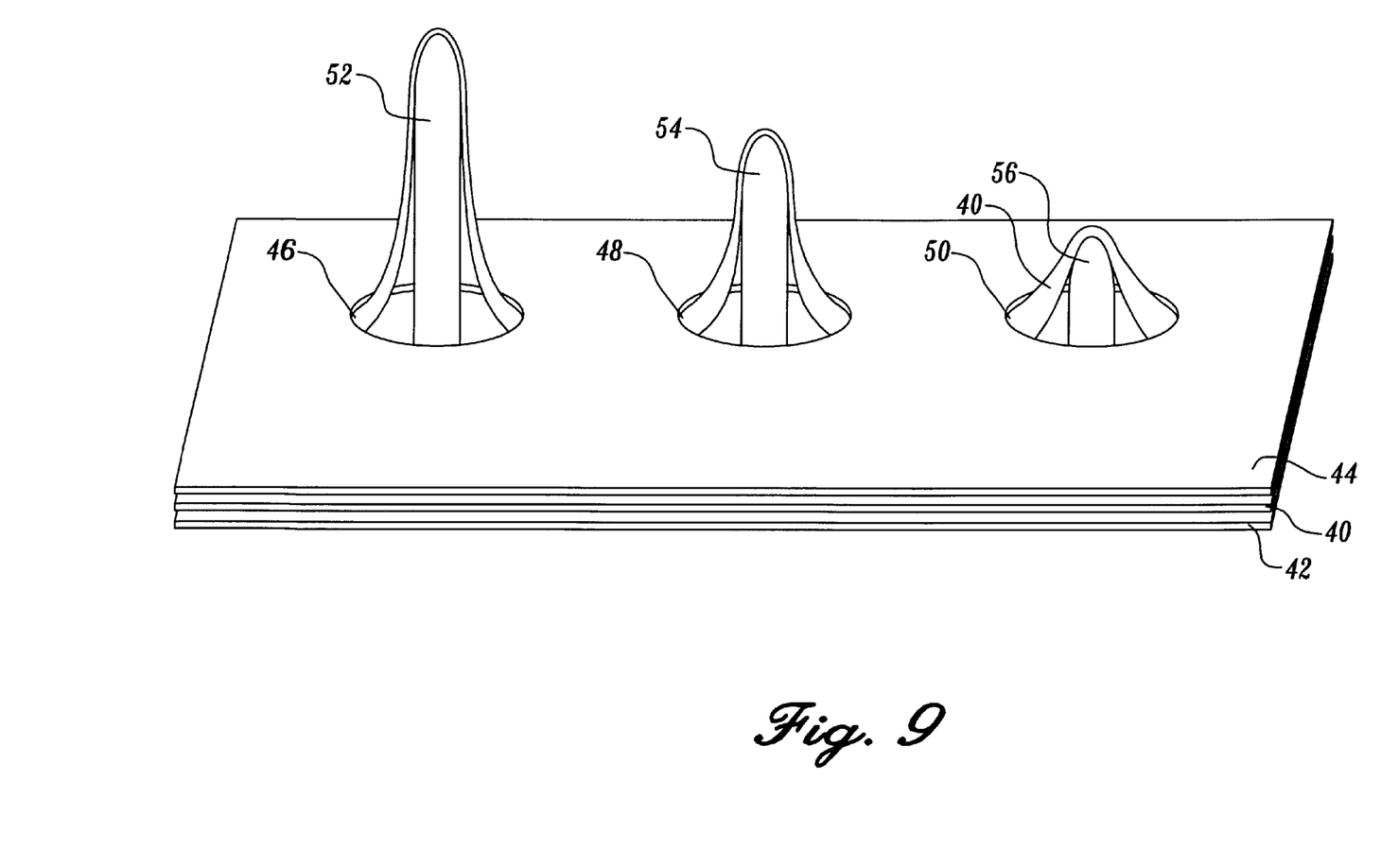
FIG. 9 shows a pictorial view of one embodiment of the present invention showing a plurality of contact rods stretching latex.
Figure 10:
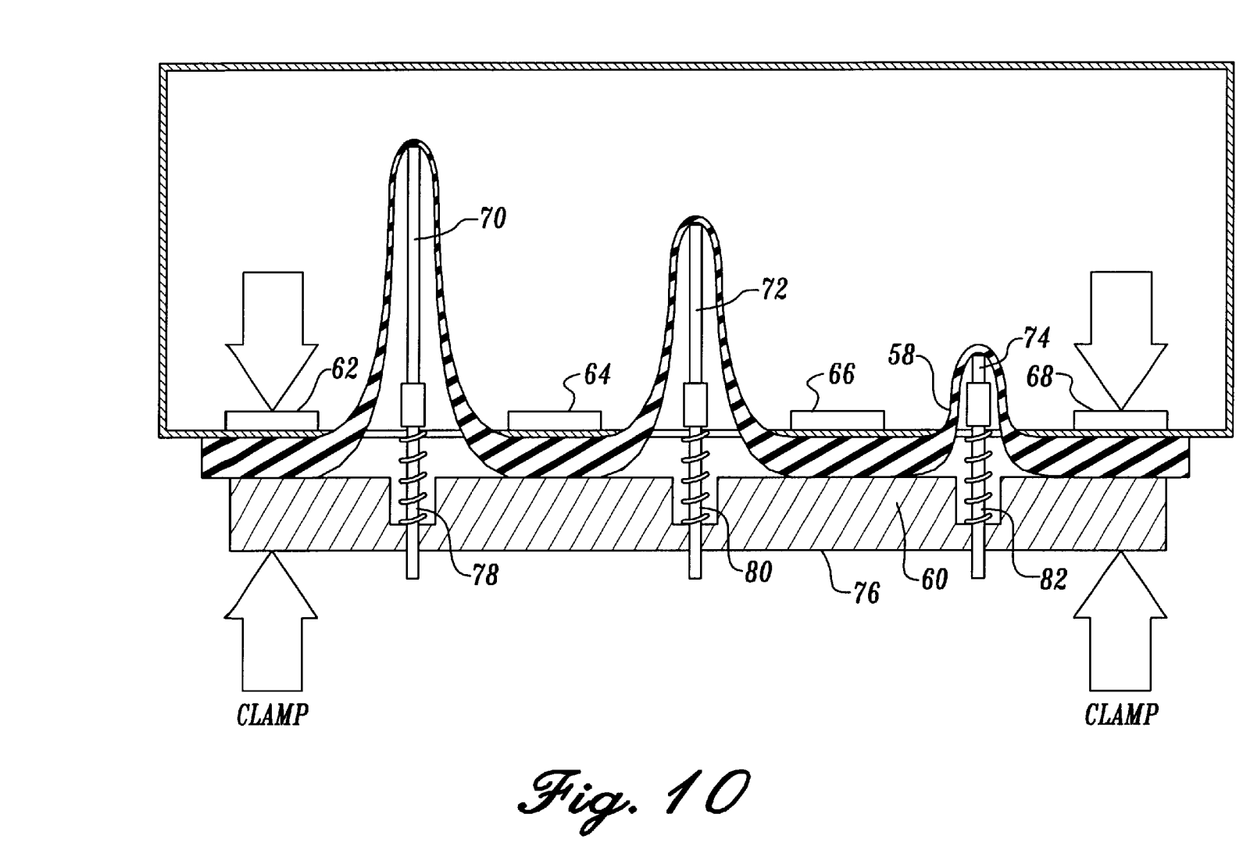
FIG. 10 shows a side view partially in cross section showing one embodiment of the invention prior to ozone exposure.
Figure 11:
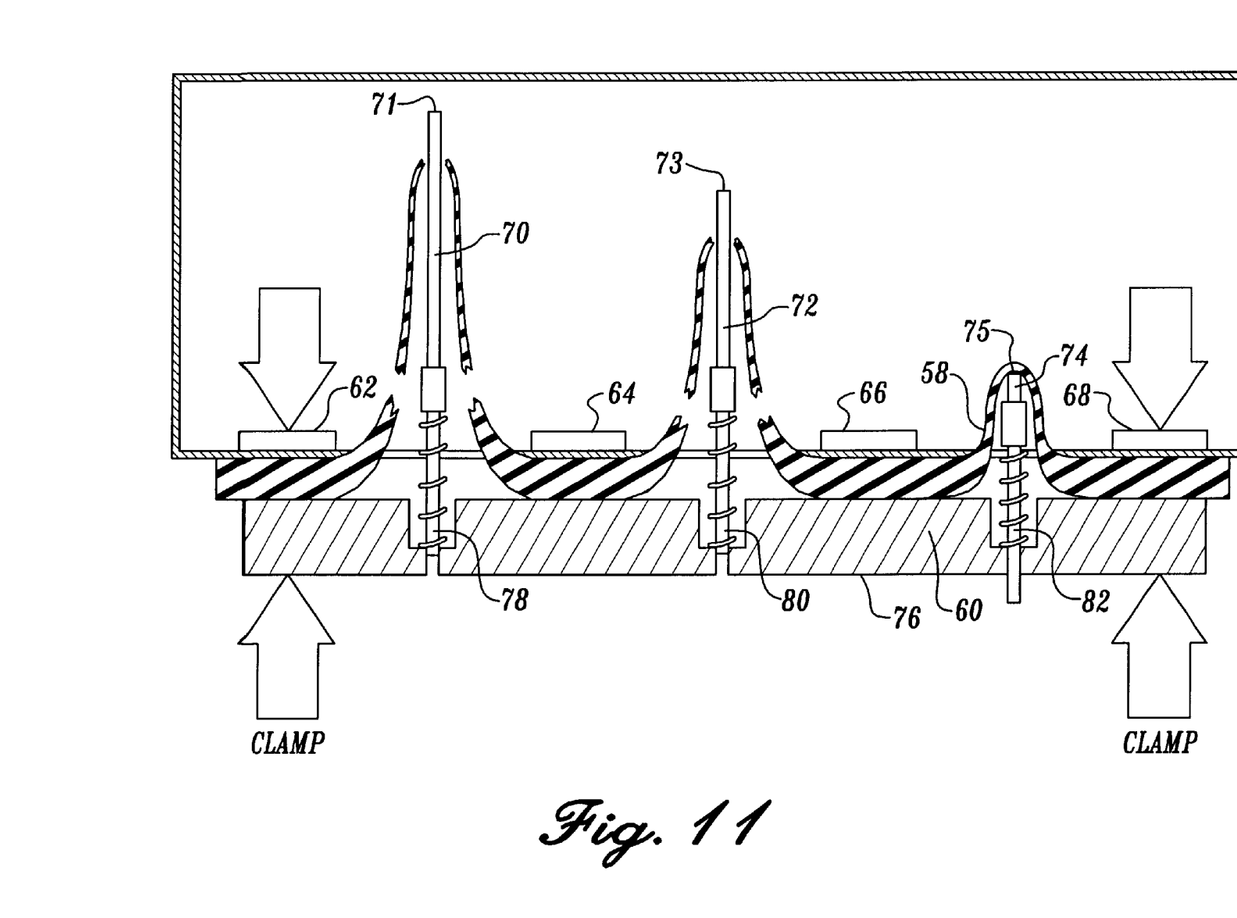
FIG. 11 shows a side view partially in cross section of the embodiment of FIG. 10 after the latex has failed.
Figure 12:
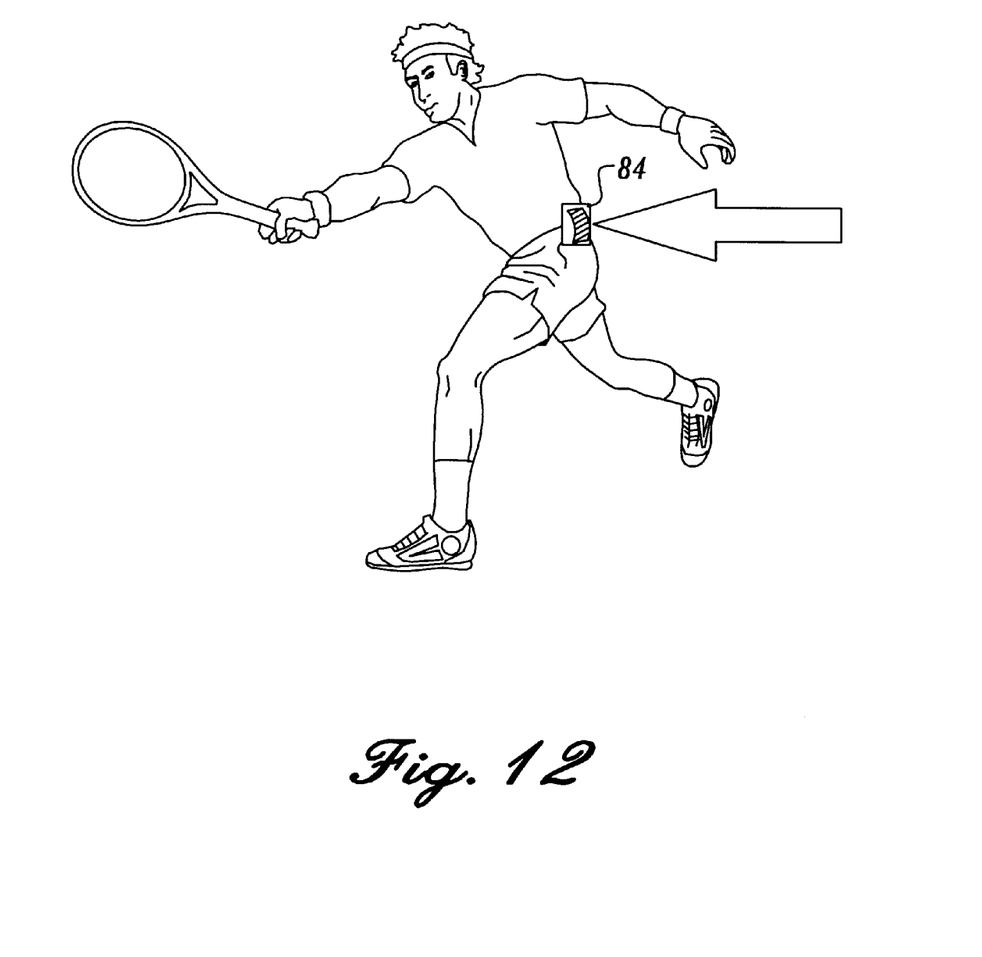
FIG. 12 shows a pictorial view of a compact portable embodiment of the present invention held on an individual's person.

Referring to FIGS. 7 through 12, an apparatus for indicating a given level of exposure to ozone can be described. Specifically, FIG. 9 shows a sheet of latex 40 sandwiched between a back plate 42 and a front plate 44. Three holes designated 46, 48, and 50 allow the latex 40 to protrude from the holes when urged to do so. Contact rods 52, 54 and 56 which are of varying lengths are used to stretch the latex 40 to different degrees when pushed through the holes 46, 48, and 50. In this arrangement the device can be placed so that the contact rods are protruding into a room being monitored. When a predetermined first ozone exposure level is reached, contact rod 52 would be expected to "break" the latex sheet 40 first within hole 46. At a greater ozone exposure level, as the latex has been stretched less relative to hole 46; the latex surrounding contact rod 54 would break. In like manner, at an even greater ozone exposure level as the latex covering hole 50 is the thickest of any of the holes, the latex covering hole 50 would break. In this way a visual indication, i.e. broken latex over a given hole would indicate a given calibrated ozone level exposure. FIGS. 10 and 11 show an alternative embodiment of the device shown in FIG. 9 wherein the contact rods can be used as visual indicators. In this Figure, a sheet of latex 58 is clamped at both ends of a plate 50, small plates 62, 64, 66, 68 secure the latex 58 to the inner side of the device in conjunction with the clamps which are not shown but functionally illustrated by the arrows at either end of the device. Contact rods 70, 72, and 74 stretch the latex 58 to varying thicknesses as shown in FIG. 9. The contact rods have contained within them indicating rods 71, 73, and 75 which protrude from the plate 60 at its outer face 76 so that when the device is viewed looking at the outer face 76 of plate 60 the ends of indicating rods 71, 73, and 75 can be seen. Springs 78, 80, and 82 are compressed by the indicating rods 71, 73, and 75 respectively. The ends of the indicating rods do positively protrude from the outer face 76 of plate 60. The other end of the indicating rod is held within the corresponding contact rod. The contact rod is made so as to have an opening in its tip so that when the situation shown in FIG. 11 occurs, namely, the breaking of the latex 58, the indicating rod is urged through the opening in the tip of the contact rod by its spring and will not be visible from the outer face 76 of plate 60. In FIG. 11, indicating rods 71 and 73 have withdrawn from protruding from plate 60 thereby indicating a predetermined calibrated ozone exposure. This device as shown in FIG. 11 can be made portable and compact and gives a clear, understandable visual indicator regarding maximum ozone level exposure in its environment. FIG. 12 shows the device designated as 84 fitted on a person while exercising.

FIGS. 7 and 8 show another embodiment of an ozone level indicator which uses O-rings. This device has a first plate 86 and a second plate 88. Pegs 90, 92, and 94 are placed on plate 86 in a staggered fashion. Plate 88 holds pegs 96, 98, and 100. O-rings 102, 104, and 106 are stretched from the pegs as shown in FIG. 7 and 8. These O-rings are of identical thickness and diameter prior to placement over the pegs. After placement over the pegs, however, O-ring 102 is stretched the greatest and therefore offers the thinnest target to any ozone present. A graduated indicator of ozone level exposure is thereby provided. FIG. 8 shows the least stretched O-ring surviving at a given ozone exposure level. This level of ozone exposure would be enough after calibration to force failure of O-rings 102 and 104 while allowing O-ring 106 to remain intact. Use of this device would, therefore, allow the determination of a range of ozone exposure levels to be indicated.

The invention may be embodied in other forms without departing from the spirit or essential characteristics thereof. The present embodiments are therefore to be considered in all respects as illustrative and not restrictive, the scope of the invention being indicated by the appended claims rather than the foregoing description, and all changes which comes within the meaning and range of equivalency of claims are intended to be embraced therein.

What I claim is:

1. Apparatus for indicating the level of exposure to ozone comprising a sheet of material which decomposes in the presence of ozone, stretching means including a contact rod which contacts said sheet of material thereby stretching said sheet to a predetermined thickness whereby failure of such material and protrusion of said contact rod indicates a predetermined level of ozone exposure.

2. The apparatus of claim 1 wherein said sheet of material which decomposes in the presence of ozone is comprised of latex.

3. The apparatus of claim 1 wherein said contact rod is supported within a plate.

4. The apparatus of claim 3 which includes spring means for allowing said contact rod to move relative to said plate when failure of said latex occurs.

5. The apparatus of claim 4 wherein said contact rod has two ends and moves from an initial position wherein one end of said contact rod partially protruding from said plate to a final position wherein said one end of said contact rod is contained within said plate after failure of said latex hereby giving a visual indication of the failure of said latex.

6. The apparatus of claim 1 wherein a plurality of contact rods are provided.

7. The apparatus of claim 6 wherein at least two of said plurality of contact rods stretch said sheet of material to different thicknesses whereby at least two different predetermined levels of ozone exposure can be indicated upon failure of said sheet of material and protrusion of said contact rods.

8. The apparatus of claim 1 which includes switch means allowing an electronic signal to be transmitted to a monitor upon failure of said sheet of material which decomposes in the presence of ozone.

9. Apparatus for indicating the level of exposure to ozone comprising a material which decomposes in the presence of ozone formed as an O-ring, a first and second plate, said first and second plate each having at least one peg attached thereon, said material formed as an O-ring being fitted over a peg of said first plate and a peg of said second plate whereby the distance between said first plate and said second plate allows the stretching of said O-ring to a predetermined thickness and failure of said O-ring indicates a predetermined level of ozone exposure.

10. The apparatus of claim 9 which includes a plurality of O-rings and a plurality of first pegs attached to said first plate and a plurality of corresponding second pegs attached to said second plate wherein the distance between the corresponding first and second pegs of said first and second plates varies thereby stretching the plurality of O-rings to different lengths allowing indication of at least two different predetermined levels of ozone exposure upon failure of said O-rings.

11. The apparatus of claim 10 wherein said material which decomposes in the presence of ozone is rubber.

12. The apparatus of claim 9 which includes switch means allowing an electronic signal to be transmitted to a monitor upon failure of said material which decomposes in the presence of ozone formed as an O-ring.

* * * * *